United States Patent [19]

Valdes et al.

[11] Patent Number: 5,676,974

[45] Date of Patent: Oct. 14, 1997

[54] PHARMACEUTICAL COMPOSITIONS CONTAINING GIROXINA AND PHOSPHOLIPASE $A_2$ AND METHODS OF INCREASING A PATIENT'S $CD_4$ COUNT USING THE PHARMACEUTICAL COMPOSITIONS

[75] Inventors: Santiago H. Valdes, Santos Dumont 2570, Buenos Aires; Diego Jose Carpintero, Kiernan Street 822, Villa Tesey, both of Argentina

[73] Assignees: Santiago H. Valdes; Diego Jose Carpintero; Jorge Leandro Marini; Alejandro Ponieman, all of, Argentina

[21] Appl. No.: 340,424

[22] Filed: Nov. 15, 1994

Related U.S. Application Data

[63] Continuation-in-part of Ser. No. 965,915, Oct. 23, 1992, abandoned.

[51] Int. Cl.$^6$ .......................... A61K 35/58; A61K 38/46; C12N 9/20
[52] U.S. Cl. ....................... 424/542; 424/94.6; 435/198
[58] Field of Search .................. 424/542, 94.6; 435/198

[56] References Cited

U.S. PATENT DOCUMENTS

| | | | |
|---|---|---|---|
| 4,341,762 | 7/1982 | Haast | 424/88 |
| 5,164,196 | 11/1992 | Plata et al. | 424/548 |
| 5,354,677 | 10/1994 | Knopf et al. | 435/198 |

*Primary Examiner*—Michael G. Wityshyn
*Assistant Examiner*—Kristin K. Larson
*Attorney, Agent, or Firm*—Beveridge, DeGrandi, Weilacher & Young, LLP

[57] ABSTRACT

Pharmaceutical compositions for treatment of humans suffering from the symptoms of acquired immune deficiency syndrome (AIDS) or its precursors, lymphadenopathy syndrome (LAS) or AIDS-related complex (ARC) or secondary diseases relating thereto and other immunodeficiency pathologies or tumors resulting exclusively from immune deficiency and others such as H.I.V. The compositions contain a therapeutically active amount of phospholipase $A_2$ and giroxina, preferably where the phospholipase $A_2$ is isolated from the venom of *Crotalus durissus terrificus* or form the venom of *Micrurus frontalis altirostris* and the giroxina is isolated from the venom of *Crotalus durissus terrificus*. Also disclosed is the process for preparing such pharmaceutical composition and the process for treating patients suffering from the aforementioned afflictions.

28 Claims, No Drawings

PHARMACEUTICAL COMPOSITIONS CONTAINING GIROXINA AND PHOSPHOLIPASE A$_2$ AND METHODS OF INCREASING A PATIENT'S CD$_4$ COUNT USING THE PHARMACEUTICAL COMPOSITIONS

REFERENCE TO A RELATED APPLICATION

This is a continuation-in-part of our application Ser. No. 07/965,915 filed Oct. 23, 1992 now abandoned, which is relied on and incorporated herein by reference.

INTRODUCTION AND BACKGROUND

The present invention relates to pharmaceutical compositions having active ingredients derived and isolated from the venom of certain snakes for treatment of humans suffering from the symptoms of acquired immune deficiency syndrome (AIDS), or its precursors, lymphadenopathy syndrome (LAS) or AIDS-related complex (ARC) or secondary diseases relating thereto, and other immunodeficiency pathologies or tumors resulting exclusively from immune deficiency and others, such as those caused by H.I.V. The present invention also relates to a process for the preparation of such pharmaceutical compositions and also to a process for the treatment of humans suffering from the above diseases by administering to such humans a therapeutically effective amount of such pharmaceutical compositions wherein the active ingredients are isolated from snake venom.

The biological activity of certain snake venoms has been recognized in the art and is known. Research to determine the composition of and the specific effect produced by the components of snake venoms has been ongoing. It has been found that snake venom contains a plurality of proteinaceous and other components or substances. Certain snake venoms or fractions thereof have exhibited therapeutical activity as anticoagulants and as analgesics.

U.S. Pat. No. 3,657,416 discloses an enzyme isolated from the venom of the snake Agkistrodon rhodostoma and the use of this enzyme for the therapeutic treatment of humans. According to U.S. Pat. No. 3,888,977, detoxified and neurotropically active modified snake venom neurotoxins (derived from a species of the Bungarus genus) are used for the treatment of progressive degenerative diseases of the nervous system which involve the function of motor nerve cells from the origin of such cells to the neuromuscular junction, as well as elements of the central nervous system including axons, nerve myelin sheaths, etc.; such diseases include amyotrophic lateral sclerosis, multiple sclerosis, kuru, polymyositis, certain meningitides, muscular dystrophy, and the like. Detoxification of the venom is performed by treatment with formaldehyde, fluorescein dyes, ultraviolet light or gentle oxygenation at relatively low temperatures.

U.S. Pat. No. 3,888,977 relates to a modified neurotoxic snake venom detoxified e.g. by oxygenation to form an atoxic, neurotropically active therapeutical composition. The venom must be at least in part derived from the genus Bungarus, but preferably also contains venoms of the genus Naja or Crotalus durissus terrificus. The composition mitigates the progress of degenerative neurological diseases by blocking nerve cell receptors.

U.S. Pat. No. 3,888,977 is, however, silent in disclosing the chemical components or composition of the modified venom. It is stated in U.S. Pat. No. 3,888,977 that the venom of snakes contains a multitude of chemical compounds including various enzymes. The exact function of the enzymes in the venom is not understood, according to the patent at column 3, and, indeed, the enzymes may not have any direct function in the toxic effect of venom. The enzymes may have other functions beneficial to the snake in utilizing the victim of its bite as food.

In U.S. Pat. No. 4,126,676, similar methods of treatment of neurological disorders are disclosed and detoxified, modified neurotoxins derived from the Naja genus of snake are used.

U.S. Pat. No. 4,341,762 discloses compositions having pharmacological activity and which contain, in an administrable form, at least one post-synaptic neurotoxin, at least one pre-synaptic neurotoxin, and at least one component capable of stimulating the immune mechanisms of the body. The post-synaptic neurotoxin component preferably contains the α-toxin obtained from the venom of an elapid snake belonging to a species of the genera Naja, Ophiophagus or Dendroaspis. The pre-synaptic neurotoxin component preferably contains β-bungarotoxin obtained from the venom of the elapid snakes Bungarus multicinctus and the component capable of stimulating the immune mechanisms of the body preferably contains a venom obtained from a viperid snake, particularly a venom obtained from a snake belonging to the family Vipera, subfamily Crotalinae.

The compositions disclosed in U.S. Pat. No. 4,341,762 may include the whole venom from which a particular activity is being sought or only a particular fraction or fractions of the venom. Thus, the pre-synaptic neurotoxin may consist of the whole venom of a Bungarus species. A whole venom from the Naja species contains post-synaptic neurotoxins which can potentially complement the pre-synaptic activity of the Bungarus component of the mixture. The component capable of stimulating the immune mechanisms of the body, the viperid component, is preferably used and is present as the whole venom since such venoms contain a plurality of enzymatic substances.

The compositions disclosed in U.S. Pat. No. 4,341,762 stimulate the production of the substance known as "interferon" or a precursor thereof. This stimulation is due to the projected presence of proteins having at least portions which resemble double-strand RNA molecular structures or which contain enzymatic activities capable of converting precursor proteins to interferon stimulating or activating agents. The compositions set forth in U.S. Pat. No. 4,341,762 are useful as antiviral and antiautoimmune agents by the stimulation of the part of the body's immune system which involves interferon or the complex activity within the body attributed to interferon. The compositions disclosed in U.S. Pat. No. 4,341,762 can be used in the treatment of the symptoms of poliomyletis, herpes simplex, herpes zoster, herpes genitalis, and diseases such as multiple sclerosis and amyotrophic lateral sclerosis and degenerative neurological disorders. The mixture of the above venoms and/or venom fractions is preferably finished in the form of solutions formed with saline solution preserved with THIMEROSAL® and are administered by injecting into the body a sterile pyrogen-free solution. The chemical structure of the composition of the components of the snake venoms or fractions thereof are not identified nor disclosed in U.S. Pat. No. 4,341,762.

The compositions set forth in U.S. Pat. No. 4,741,902 are an improvement of those disclosed in U.S. Pat. No. 4,341,762. These compositions also contain effective amounts of at least one post-synaptic neurotoxin and at least one pre-synaptic neurotoxin, but the component capable of stimulating the immune mechanisms of the body is the viperid "b"

fraction obtained from elution of the viperid venom on SEPHADEX® G-50 column in place of the whole viperid snake venom. The composition is allegedly useful in the treatment of the diseases enumerated in U.S. Pat. No. 4,341,762. The venom fraction obtained after elution on a SEPHADEX® G-50 column is free of certain enzymes such as L-amino acid oxidase and phosphodiesterase, and this imparts particular utility to the composition due to the absence of a hemorrhagic effect when used in the treatment of mammals U.S. Pat. No. 5,002,766 is directed to a method of treating a patient having acquired immune deficiency syndrome (AIDS) or its precursors, lymphadenopathy syndrome (LAS) or AIDS-related complex (ARC), by administering a composition comprising trypsin, α-chymotrypsin, papain, pancreatin, bromeline, lipase, amylase and rutin. According to the disclosure of the patent, the above catabolic enzymes show unexpected successes in the improvement of the condition of the patients suffering from AIDS or precursors or secondary diseases related thereto.

It is known that acquired immune deficiency syndrome (AIDS) and its precursors are caused by a retrovirus called human immunodeficiency virus (HIV). Infection with HIV disturbs the whole immunodefense mechanism of the human organism, first of all by affecting the key positions of immunodefense, namely the helper cells of the T system. Such T4 (helper) cells affected by the infection with HIV are no longer capable of performing their central role in the regulation of the immunoresponse. The disturbing effect caused by infection with HIV is the result of a direct or indirect reduction of the T4 (helper) cells.

Infections with HIV result in disturbances of the equilibrium between the different T cell populations. Thus, the balance between the T4 (helper) and T8 (suppressor) cells is changed and is shifted in favor to the T8 cells at the expense of the T4 cells. As a result, the T4/T8 ratio, being generally about 1.4 to 2, is shifted to a T4/T8 ratio of 1:2 or even lower values. The HIV-induced reduction of the T4 cells allows pathogenic organisms (e.g., viruses, bacteria, fungi or protozoans), which are harmless in case of a normal balance between the different T cell populations, to meet with favorable conditions in patients having the above disproportion between T4 and T8 cells. Persons suffering from AIDS may be subject to attack by different pathogenic organisms and carcinomatous degenerations of tissue (e.g., Kaposi sarcoma) and also may be subject to attack by other malignant diseases.

AIDS is one of the most serious menaces to mankind. Although various drugs and treatment have been developed, none of them provides any significant success against the affliction.

SUMMARY OF THE INVENTION

It is an object of the present invention to provide a pharmaceutical composition which mitigates the symptoms of AIDS or its precursors (LAS or ARC) or secondary diseases related thereto or other immune-deficiency-pathologies or tumors resulting exclusively from immune deficiency and others such as HIV, and keeps patients suffering from the above diseases symptom-free for a longer period of time. The main field of application of the composition according to the present invention is the treatment of patients suffering from the symptoms of AIDS.

It is a further object of the present invention to provide a method of treatment which mitigates the symptoms of AIDS or its precursors (LAS or ARC) or secondary diseases related thereto or other immune-deficiency-pathologies or tumors resulting exclusively from immune deficiency and others such as HIV, and keeps patients suffering from the above diseases symptom-free for a longer period of time.

According to an aspect of the present invention, there is provided a pharmaceutical composition for treatment of humans suffering from acquired immune deficiency syndrome (AIDS) or its precursors, lymphadenopathy syndrome (LAS), or AIDS-related complex (ARC), or secondary diseases related thereto or other immunodeficiency-pathologies or tumors resulting exclusively from immune deficiency and others such as HIV, comprising a therapeutically active amount of phospholipase $A_2$ and giroxina in admixture with suitable inert pharmaceutical carriers or diluents.

According to a further aspect of the present invention, there is provided a process for the preparation of a pharmaceutical composition for the treatment of humans suffering from acquired immune deficiency syndrome (AIDS), or its precursors lymphadenopathy syndrome (LAS) or AIDS-related complex (ARC), or a secondary disease related thereto, or other immunodeficiency-pathologies or tumors resulting exclusively from immune deficiency and others such as HIV, comprising admixing a therapeutically active amount of phospholipase $A_2$ and giroxina with suitable inert pharmaceutical carriers or diluents.

According to a still further aspect of the present invention, there is provided a method of treatment of a patient suffering from acquired immune deficiency syndrome (AIDS), or its precursors, lymphadenopathy syndrome (LAS) or AIDS-related complex (ARC), or secondary diseases related thereto or other immunodeficiency-pathologies or tumors, resulting exclusively from immune deficiency and others such as HIV, comprising administering to the patient in need thereof a composition comprising a therapeutically active amount or phospholipase $A_2$ and giroxina in admixture with an inert pharmaceutical carrier or diluent.

DESCRIPTION OF THE PREFERRED EMBODIMENTS OF THE INVENTION

The phospholipase $A_2$ component of the composition according to the present invention is an enzyme (Enzyme Code 3.1.1.4) which is also denominated as phosphatydil 2-acyl hydrolase or Lecitinase A. Phospholipase $A_2$ may be isolated from the dried poison of *Crotalus durissus terrificus* (cascabel of Argentina). It is designated in the International Catalogue Sigma Chemical Company, Biochemical Organic Compounds (for Investigation and Diagnostic Reagents), U.S.A. and Canada, at page 812 of Edition 1990 and at page 841 of Edition 1991 as "Product No. 5910". Phospholipase $A_2$ appears as a lyophilized dust containing 50% of proteins (standardized by the Biset method) and has an activity of 200 U.V. times per mg., at pH 8.9 and 25° C., using as substrate L-A Phosphatydil choline of soya. Phospholipase $A_2$ can also be isolated from the dried poison of *Micrurus frontalis altirostris*, a coral snake of Argentina.

The giroxina component of the composition according to the present invention is a basic polypeptide, molecular weight 3000 daltons, pH 10 containing four sulfur bridges. Giroxina was first disclosed to be contained in the so-called "Crotoxina Complex" (Slotta and Frankel-Conrat: Chemical Studies on Ofidios Venoms (1038–39), Accounts of the Butantan Institute, Volume 12, pages 505–513). Crotoxina complex is described as having a molecular weight of 33,000 daltons. Later it turned out that the basic component Crotoxina actually contains was "Crotamina", a basic polypeptide, pH 10.3, molecular weight 5430 daltons, containing four sulfur bridges.

Crotoxina is also disclosed to be a complex containing an acidic protein (pH 3.7, molecular weight 9000 daltons) and a basic: protein (pH 8.65, molecular weight 12,000 daltons). The total molecular weight of Crotoxina is set forth to be 21,000 daltons.

Alexander VRS Voet described in his book entitled "The Why, When and How of Ophibians (snakes)", published in 1985 by the Editorial American Lee Publishing House (Argentina), on page 423, that giroxina is a basic polypeptide with a molecular weight of 3,000 daltons, pH 10, and having four sulfur bridges. It was disclosed, however, to be just a minimal fraction of the complete venom complex and no pharmaceutical utility of giroxina is set forth in the book.

Giroxina can be isolated from the dried snake venom of *Crotalus durissus terrificus*.

Phospholipase $A_2$ and giroxina can be readily isolated from the dried venom of *Crotalus durissus terrificus*. The isolation of these components and the separation thereof from other enzymes, proteins and polypeptides present in the venom. (many of which are toxic) is based on the thermal stability of phospholipase $A_2$ and giroxina.

The fresh venom *Crotalus durissus terrificus* obtained by direct extraction is desiccated with the aid of a vacuum pump and/or in the presence of a dehydrating agent (e.g., calcium chloride). Desiccation is carried out at a temperature at which the majority of the other components (enzymes, neurotoxins, etc.) present in the fresh venom are destroyed by decomposition. A preferable temperature is 65° C. The desiccated residue is a crystalline or pseudocrystalline powder.

The weight ratio between phospholipase $A_2$ and giroxina is within the range of 20:1 and 4:1, preferably between 8:1 and 9:1. According to a particularly preferred embodiment of the present invention, the weight ratio of phospholipase $A_2$ and giroxina is about 8.1:1.

The pharmaceutical compositions of the present invention may contain any suitable pharmaceutical carriers or diluents known to the art. It has been found to be advantageous to use a sodium chloride solution as diluent. The concentration of the sodium chloride solution may be preferably about 0.17 mole/liter. The sodium chloride solution may preferably contain a conservator. Any suitable conservator (e.g., THIMEROSAL®) being inert to the active ingredients may be used.

The pharmaceutical compositions according the present invention may optionally contain further components which strengthen the activity of the composition. For this purpose tioctic acid, magnesium lactate and/or $B_6$ vitamin may be used.

The composition according to the present invention may be preferably prepared by dissolving phospholipase $A_2$ and giroxina in the weight-ratio disclosed above in a sodium chloride solution which contains a conservator. Dissolving is performed at a suitable temperature to dissolve the desired components, preferably at 76° C. The solution is stirred as the components enter into solution. The solution thus obtained is placed into vials and the vials are hermetically sealed.

The composition according to the present invention is preferably administered subcutaneously, though other routes of administration are possible (e.g., sub-lingual). The daily dosage depends on the seriousness of the disease and of the condition of the patient and is not related to the patient's weight. A preferred daily dose amounts to 0.10–0.30 ml of the solution prepared according to Example 1, infra. It is recommended to administer 0.15–0.18 ml as maintenance dose to patients who have recovered their normal weight. 0.10 ml would be administered to those patients having CD4 counts of >700 and <1200. On starting treatment of patients highly affected by AIDS virus, it is expedient to use a dose of 0.3 ml for at least 30 days ("highly affected" is defined as those AIDS patients to are in an advanced state of sickness or with advanced symptoms of sickness, technically measurable by the quantity of CD4 lymphocytes (i.e., less than 700 CD4 lymphocytes, which is below the normal range of 1200–1400)); the dosage may be reduced by 0.05 ml per month as the CD4 count increases. In more serious cases double (200%) of the above amounts may be administered. The treatment is to be carried out daily at least for 60–90 days, and the patient's condition is checked every 20–25 days by means of clinical and laboratory controls. If necessary the daily treatment may be continued up to a total period of 120 days or more (days 91–120).

The pharmaceutical composition of the present invention when kept in a refrigerator at a temperature of +4° C. maintains its biological activity for at least 120 days. Freezing alters the active ingredients and therefore the composition should not be subjected to freezing.

Without being bound by theory, it has been found that the composition of the present invention does not act on the virus or tumor but unexpectedly induces an energic hypothalamic stimulation and actually causes a "hypothalamic shock" which results in a feeling of well-being (e.g., disappearance or decrease in pain, discomfort, adenopathies, loss of weight, and depression) and an increase of the immunoindividual-response (i.e. number of CD4 lymphocytes), allowing an excellent response with great and successful potential. In contrast to other drugs used in the treatment of AIDS, the composition according to the present invention does not act directly against the viruses or on the natural operators of the immune-lymphocytes-response (macrophagues, histiocytes, etc.), but exerts its effect on the hypothalamus - - - i.e., on the "orchestra director" of the immune system - - - making the individual able to defend himself from the viral attack, until the virus' pathogenic capacity is exhausted.

A further advantage of the composition of the present invention over drugs hitherto used in the treatment of AIDS (e.g., AZT, interferon, Timoduline) is that the favorable effects of the inventive composition are not followed by further attacks which can be even more serious for the immunity deficiency. The effect on the individual of the composition according to the present invention is continuous, often lasting several months (between 90 and 120 days) after the completion of the treatment.

A further significant advantage of the composition of the present invention resides in the absence of serious side-effects, which are characteristic of the hitherto known drugs, especially of AZT. The pharmaceutical composition of the present invention may only cause a light rubefaction and temporary irritations in the areas of application if it is used in the above recommended doses or in doses up to 100 or 200% of the suggested amount, which increased doses may be necessary in some cases. No serious secondary effects or side-effects were observed.

Since the composition of the present invention can not be applied simultaneously with cortisone or similar drugs, it is a non-aggressive therapy and thus the effects of aggressive therapies (e.g., surgical, chemotherapy, etc.) can be diminished. The inventive composition is perfectly compatible with analgesics, antibiotics, etc.

The composition of the present invention was tested in several hundred patients suffering from AIDS or precursors or secondary diseases related thereto. Hereinafter the results of these clinical tests are briefly summarized.

The composition of the present invention prepared as described in Example 1 exclusively was administered subcutaneously to several hundred patients suffering from tumors resulting from immune deficiency and others, such as those caused by HIV as an alternative therapy for the treatment of tumors. A favorable reaction and cessation of future growth was found in about 80% of the cases while in about 40% of the treated cases a complete cure was observed. In those cases with a positive response, the pharmaceutical composition of the invention did not act on the tumor but rather on the immune system. It can be inferred that these tumors were neoplasies due to immunity deficiencies because of shocks and/or stress of different origin depending on the patients psycho-immunepathologies.

In another clinical test-series 10 patients suffering from AIDS were treated subcutaneously with the composition prepared according to Example 1. Six of these patients were addicts and four homosexuals or bisexuals. All patients showed positive ELISA, positive Western-Blot, with poor general physical conditions and T lymphocytes recount CD4 (cluster denomination four) between 130 and 200.

The application of the composition prepared according to Example 1 in the treatment period of 40 days resulted in the increase of CD4 to 1300–1400 with a remarkable improvement of the general health condition of the patients so that it could be assumed that the new population of T lymphocytes was not infected.

Ninety days after the application of the treatment seven out of the 10 patients showed negative Western-Blot, with normal recount of CD4 and excellent general conditions (e.g., a state of well being which did not exist when the treatment began; disappearance of prior symptoms of pain, discomfort, adenopathies, etc.). The seven patients appeared as if they never had AIDS.

One of the parameters of AIDS diagnosis is the recount of CD4 (cluster denomination four). In normal health conditions the CD4 value amounts to 1400–1500, in serious cases it is 800–400 and in very serious cases it is decreased to under 300.

Another characteristic parameter of the AIDS diagnosis is the Western-Blot (W.B.) which is negative in healthy persons but positive in persons having AIDS.

In another clinical test-series 100 patients suffering from AIDS were treated subcutaneously with the composition of Example I. Clinical recuperations wherein the CD4 increased to a normal count, and the Western-Blot was negative, were observed in such patients.

The aforesaid are just of an illustrative character to show the scope and effectiveness of the present invention. However, it is to be understood that within the scope of the invention as indicated herein, the invention may be practiced in ways other than explicitly described hereinabove without departing from the intended scope of the invention. It is by no means intended to limit the scope of the present patent application to the above disclosure.

EXAMPLE 1

0.00324 g of phospholipase $A_2$ obtained from the dried venom of *Crotalus durissus terrificus* and 0.0004 g of giroxina obtained from the same snake venom were dissolved while stirring in 20 ml of a 0.17 molar sodium chloride solution containing 1 ml of a 0.1% phenol solution (or another suitable preservative known in the art such as 0.1% THIMEROSAL) formed in a 0.17 molar sterilized sodium chloride solution under gentle stirring at a temperature of 76° C. for 30 minutes; such a small amount of phenol would not be harmful. The solution thus obtained was placed in a vial of 25 ml capacity made of transparent glass, stoppered with a hermetic rubber cover and provided with an additional aluminum cover.

EXAMPLES 2–9

These Examples comprise the synopsis of 8 clinical histories randomly selected from more than 100 case histories. In Table 1, the patients (suffering from AIDS and testing positive for HIV) are identified by their initials, their sex and age, their previous symptoms, the method of treatment (dosage of SIIF and frequency), and the results experienced. The evolution of the condition of the patients is disclosed as well.

TABLE 1

SICK PATIENTS WITH AIDS TREATED WITH SIIF[2], WHO COMPLETED 120 DAYS OF TREATMENT

| DATE | SEX AND AGE | | PREVIOUS SYMPTOMS | LABORATORY | SIIF[3] | RESULT | STATUS AS OF MARCH 1992 |
|---|---|---|---|---|---|---|---|
| 03/87 | M | 66 | Fever, Depression, Asthenia, Polyadeno- | Elisa[4] + WB + | 0.30 mil. | Elisa − | Clinical cured. |
|  | O.S. |  | pathies. (Addict) | C.D.4 200 | 120 days | C.D.4 800 | (More than 5 years of treatment) |
| 04/87 | M | 49 | Mononucleosis, Polyadenopathies. | Elisa + WB + | 0.30 mil. | Elisa − | Clinically cured. |
|  | B.G. |  | (Homosexual and Drug addict) | C.D.4 250 | 120 days | C.D.4 700 | (More than 5 years of treatment) |
| 05/87 | M | 58 | Depression, Diarrhea, Loss of Weight, | Elisa + C.D.4 280 | 0.30 mil. | Elisa − | Clinically cured. |
|  | R.D. |  | Asthenia. (Homosexual) |  | 120 days | C.D.4 650 | (More than 5 years of treatment) |
| 05/87 | F | 18 | Polyadenopathies, Depression. (Addict) | Elisa + C.D.4 300 | 0.30 mil. | Elisa − | Clinically cured. |
|  | C.L. |  |  |  | 120 days | C.D.4 750 | (More than 5 years of treatment) |
| 06/87 | F | 29 | Loss of weight, Diarrhea, Fever, Depression. | Elisa + C.D.4 290 | 0.30 mil. | Elisa − | Clinically cured. |
|  | A.M. |  | (Addict) |  | 120 days | C.D.4 700 | (More than 5 years of treatment) |
| 07/87 | M | 36 | Convulsions. Asthenia, Diarrhea. Poly- | Elisa + WB + | 0.30 mil. | Elisa − | Clinically cured. |
|  | L.G. |  | adenopathies. (Homosexual) | C.D.4 310 | 120 days | C.D.4 800 | (More than 5 years of treatment) |

TABLE 1-continued

SICK PATIENTS WITH AIDS TREATED WITH SIIF[2], WHO COMPLETED 120 DAYS OF TREATMENT

| DATE | SEX AND AGE | PREVIOUS SYMPTOMS | LABORATORY | SIIF[3] | RESULT | STATUS AS OF MARCH 1992 |
|---|---|---|---|---|---|---|
| 08/87 | F 30 M.F. | Depression, Stress, Cephalalgia. Asthenia. (Homosexual and Addict) | Elisa + C.D.4 320 | 0.30 mil. 120 days | Elisa − C.D.4 730 | Clinically cured. (More than 5 years of treatment) |
| 02/88 | M 31 C.A. | Psychotic conduct. Polyadenopathy. Notable Loss of Weight. (Bisexual and Addict) | Elisa + WB + C.D.4 400 | 0.30 mil. 120 days | Elisa − C.D.4 700 | Clinically cured. (More than 5 years of treatment) |

[2]NON-SPECIFIC IMMUNOGENIC FACTOR STIMULATOR.
[3]NON-SPECIFIC IMMUNOGENIC FACTOR STIMULATOR.
[4]ELISA = enzyme-linked immunosorbent assay.

In the first column of Table 1, the date refers to the month treatment began. The second column refers to the sex, age and initials of the patients. In the third column, the symptoms of the patients at the beginning of treatment are shown. The fourth column refers to laboratory data at the beginning of treatment. In the fifth column, the first 120 days of treatment are referred to (the entry of "0.30 mil. 120 days" means 0.30 ml of the composition prepared according to Example 1 administered daily for 120 days, "SIIF" refers to "Stimulator Immunogenic Inespecific Factor" (the composition of the present invention)). The sixth column shows laboratory results after the treatment in the fifth column. In the seventh column, "Clinically cured" means that CD4 counts increased to normal by March 1992 with repeated treatments (0.30 mil. 120 days) at least once a year.

The following are Elisa results for the patients in

TABLE 1

| Patient initials | Date | Elisa results* |
|---|---|---|
| O. S. | 3/5/87 | positive |
| O. S. | 7/6/87 | negative |
| B. G. | 4/12/87 | positive |
| B. G. | 8/15/87 | negative |
| R. D. | 5/20/87 | positive |
| R. D. | 9/12/87 | negative |
| C. L. | 6/3/87 | positive |
| C. L. | 10/2/87 | negative |
| A. M. | 6/10/87 | positive |
| A. M. | 10/10/87 | negative |
| L. G. | 7/5/87 | positive |
| L. G. | 11/5/87 | negative |
| M. F. | 9/5/87 | positive |
| M. F. | 1/10/88 | negative |
| C. A. | 2/14/88 | positive |

TABLE 1-continued

| Patient initials | Date | Elisa results* |
|---|---|---|
| C. A. | 6/12/88 | negative |

*Investigation of IgG specific antibodies against HIV (HTLV-III-LAV), antigens are "Env" and "Core" proteins obtained by means of recombinant DNA

EXAMPLE 12-21

These examples present 10 cases which were randomly selected from 119 case histories. The patients (suffering from AIDS and testing positive for HIV) in Table 2 are again designated by their initials, their age and sex, the laboratory results obtained prior to treatment (column 5) and the clinical aspects before treatment (column 6). The treatment control results, the clinical observations and the general observations are disclosed as well. In the column headed "Treatment" the term "0.30 ml. (daily) 60 days" means "0.30 ml of the composition prepared according to example 1 administered daily for 60 days; the numbers "0.18 ml", "0.20 ml" and "0.25 ml" are to be interpreted accordingly. The term "no control by patients' reasons" means that the patient did not agree to the implementation of necessary controls (e.g., CD4 counts, ELISA, and Western-blot). In the fifth column, ELISA followed by a number or "several" means that more than one ELISA was conducted. In columns 8–11, the number of days refers to the number of days after initiation of therapy. In columns 8–9, all "ELISA" indicated were positive. "W. tried classification" refers to Western-blot counts.

TABLE 2

SUMMARY OF 10 CLINICAL HISTORIES RANDOMED FROM 119 CASES TREATED WITH THE PRODUCT PREPARED ACCORDING TO EXAMPLE 1 AGAINST A.I.D.S.

| EXAMPLE NO. | CODE: NAME | AGE SEX | W. TRIED CLASSIFI-CATION | LABORATORY PREVIOUS RESULTS | CLINICAL ASPECTS PREVIOUS | TREATMENT S.I.I.F. | CONTROL 30 DAYS | CONTROL 60 DAYS | CONTROL 90 DAYS | CONTROL CONTROL 120 DAYS | UNTIL MARCH '92 | CLINICAL EVALUATION | OBSERVATIONS |
|---|---|---|---|---|---|---|---|---|---|---|---|---|---|
| 12 | R.F.B. | 42 M | 3 | ELISA + WB + $CD_4$ 400 | Limpha-denopathie, Diarrhea, Fever | 0.30 ml. (Daily) 60 days | ELISA WB + $CD_4$ 900 | ELISA WB + $CD_4$ 1100 | WB – $CD_4$ 1300 | X | WB – — | Highly Favorable | Addict |
| 13 | M.B. | 23 M. | 3 | ELISA (2) – WB + CD4 300 | High Fever, Loss of Weight, Neuro-pathie | 0.30 ml. (Daily) 120 Days | ELISA WB + $CD_4$ 500 | ELISA WB + $CD_4$ 1000 | X | WB – CD 1400 | WB – — | Highly Favorable | Homosexual |
| 14 | S.Z. | 50 M | 2 | ELISA + $CD_4$ 400 | Fever, Limpha-denopathie | 0.30 ml. (Daily) 60 Days | WB + — | WB + $CD_4$ 900 | X | WB – $CD_4$ 1300 | X | Highly Favorable | Homosexual |
| 15 | J.C.D. | 22 M | 4 | ELISA (3) + WB + $CD_4$ 180 | Fever, Neuro-phobic, High Loss of weight | 0.18 ml. 30 days 0.25 ml. 60 days | WB + $CD_4$ 200 | WB + $CD_4$ 600 | WB + $CD_4$ 1100 | WB – $CD_4$ 1400 | X | Clinically Good Health | Addict Bi-Sexual |
| 16 | M.P.B. | 51 F | 2 | ELISA $CD_4$ 500 | Limpha-denopathie, Fever | 0.30 ml. 60 days (Daily) | WB + $CD_4$ 900 | X | WB + $CD_4$ 1200 | X | X | Clinically Good Health | Addict |
| 17 | J.A. | 32 M | 3 | ELISA + WB + $CD_4$ 400 | Neuro-pathie, Fever | 0.30 ml. 90 Days (Daily) | X — | ELISA + $CD_4$ 1100 | WB + $CD_4$ 1400 | WB + | X | Highly Favorable | — |
| 18 | T.F.G. | 59 M | 5 | ELISA + (Several) WB + $CD_4$ 200 | High Loss of Weight, Limphadeno-pathie, Oral Candiasis | 0.20 ml. 40 Days; 0.30 ml. 80 Days | WB + $CD_4$ 400 | WB + $CD_4$ 600 | WB + $CD_4$ 1000 | WB + $CD_4$ 1400 | WB – — | Clinically Good Health | Addict |
| 19 | J.R. | 63 M | 2 | ELISA + $CD_4$ 500 | Fever, Persistent Limpha-denopathie | 0.30 ml. 30 Days | WB + $CD_4$ 900 | X | X | X | X | Insufficient Control | Bi-Sexual |
| 20 | A.A.N. | 19 M | 3 | WB + $CD_4$ 600 | Diarrhea, Persistent Fever, flush | 0.25 ml. Daily 40 Days | ELISA + WB + $CD_4$ 600 | WB + $CD_4$ 1000 | WB – $CD_4$ 1300 | X | X | Clinically Good Health | Homosexual |
| 21 | E.B. | 60 F | 3 | ELISA + WB + $CD_4$ 400 | Neurosie, Fever, Herpes | 0.30 ml. Daily 60 Days | WB + $CD_4$ 700 | X | WB + $CD_4$ 1300 | X | X | Clinically Good Health | — |

— = NOT MEASURED
X = NO CONTROL BY PATIENTS' REASONS

The results of Table 2 clearly show the efficiency of the treatment with the pharmaceutical composition according to the present invention. The Western-Blot (WB) became negative and the CD$_4$ value increased significantly. The clinical evaluation of the patients after treatment was generally highly favorable, and the patients were clinically in good health.

TABLE 3

SOLID AND LIQUID TUMORS TREATED WITH S.I.I.F. BETWEEN 1984 AND 1994
IN THESE TEN YEARS, MORE THAN 120 CASES
WE ACHIEVED 75% CLINICALLY CURED OR STABLE, AND 25% FATALITIES
WE REFER TO 25 CASES UNDER OUR CONTROL TO DATE WHICH WE CONSIDER CLINICALLY CURED

| DATE | AGE SEX | DIAGNOSIS | DOSAGE AND TIME OF TREATMENT | CONTROL 60 DAYS | CONTROL 90 DAYS | PRESENT STATUS AS OF MAY, 94 |
|---|---|---|---|---|---|---|
| 6/84 | 55 M | CA of right lung | 0.30 120 days operated 7/84 | good recovery | | presently cured |
| 3/85 | 40 F | breast CA | 0.30 120 days operated 4/85 | good recovery | | presently cured |
| 4/86 | 50 | CA of colon | 0.30 150 days operated 5/86 re-operated 11/87 | good recovery | | presently cured |
| 6/87 | 45 M | osseous CA of femur | 0.30 120 days | good recovery | | presently cured |
| 8/87 | 70 M | primitive stomach CA | 0.30 95 days | good recovery repeat SIIF 30, 40 days | | presently cured |
| 2/88 | 80 M | multiple CA of colon over diverticul. | 0.30 120 days | good recovery | | cured. died 11/93 at 85 cardiopathy |
| 2/88 | 59 M | primitive CA of tibia | 0.30 120 days | good recovery | | presently cured |
| 2/88 | 60 F | breast CA | 0.30 120 days operated 12/88 | good recovery | | presently cured |
| 4/89 | 49 F | CA metastasis of humerus (CA opp. breast) | 0.30 120 days | good recovery | | presently cured |
| 6/89 | 48 M | epidermoid CA of vocal chords | 0.30 120 days | good recovery | | presently cured |
| 3/90 | 70 F | lymphoid leukemia | 0.30 120 days | advance disease disease slowed weight recovered leukocytes at 10,000 | | clinically cured at present |
| 4/90 | 59 M | osseous prim. CA of iliac | 0.30 120 days | developing favorably | | stable |
| 6/90 | 47 M | prim. CA of femur | 0.30 120 days | developing favorably | | presently cured |
| 6/90 | 60 M | CA of the bladder | 0.30 120 days operated 7/90 | developing well | | clinically cured |
| 7/90 | 64 M | CA of the prostate | 0.30 120 days operated 8/90 | developing favorably | | clinically cured |
| 2/91 | 40 F | CA of the uterus | 0.30 120 days | developing favorably | | stable |
| 3/91 | 55 F | CA of the breast | 0.30 120 days | developing favorably | | clinically cured |
| 6/92 | 50 M | CA of the colon | 0.30 140 days operated 8/92 re-operated 2/93 | developing favorably | | presently cured |
| 6/92 | 20 M | CA of the testicles seminoma | 0.30 120 days | operated tumor good recovery | | stable |
| 7/92 | 49 F | CA of the stomach | 0.30 120 days | refused operation developing favorably | | stable |
| 2/93 | 40 M | CA of the lungs | 0.30 120 days | operated 4/93 good recovery | | stable |
| 2/93 | 40 F | CA of the tip of the uterus | 0.30 120 days | operated 3/93 good recovery | | stable |
| 3/93 | 48 | recurrent CA of the breast operated | 0.30 120 days | good recovery | | clinically cured |
| 4/93 | 75 M | CA of the lungs | 0.30 120 days | good recovery | | stable |
| 5/93 | 45 M | CA of the skin epithelium | 0.30 120 days | operated 6/93 developing favorably | | stable |

In Table 3, the "date" is the date that treatment began. "Control 60 days" and "Control 90 days" refers to days after initiation of therapy. "Cured" means that the tumor is no longer present. For the fifth patient, the table states that SIIF was repeated 30, 40 days which means that administration of SIIF was repeated after 30–40 days. "Operated" means that the patient had an operation to remove the tumor. "Stable" means that the patient had no negative symptoms (i.e., the patient had no symptoms due to the disease). "CA" means cancer. "0.30 120 days" means 0.30 ml of the composition prepared according to Example 1 administered daily for 120 days.

TABLE 4

TREATMENT WITH S.I.I.F. ON PATIENTS WITH ACQUIRED IMMUNODEFICIENCY SYNDROME (AIDS) TWENTY-TWO CASES OF ACQUIRED IMMUNODEFICIENCY SYNDROME (AIDS) HAVE BEEN TAKEN. SEVEN OF THEM TREATED SINCE 1987 AND THE OTHER FOURTEEN SINCE 1988 UNTIL THE PRESENT OF THE 200 CASES TREATED, 70% ARE CLINICALLY CURED AND 30% HAVE DIED (7% SUICIDES, 15% TUBERCULOUS MENINGITIS, 8% PNEUMONIA) IN ALL CASES WE ADDED THIOCTIC ACID, AND IN THE CASE OF INFECTIONS, BACTERIN AND ISONIAZID, ANTI-DIARRHEAL, AND IN DEPRESSIONS, IMPRAMIN WE DID NOT EMPLOY A.Z.T., D.D.C. OR D.D.I. (ALTHOUGH THE MAJORITY OF THE PATIENTS HAD TAKEN THOSE MEDICATIONS PREVIOUSLY) FINALLY, WE MUST CLARIFY THAT AFTER 120 DAYS, 40%, STABLE UNTIL THAT CONTROL POINT, FAIL TO RETURN

| DATE | AGE SEX | CLINICAL AND LABORATORY ASPECTS | S.I.I.F. TREATMENT DOSAGE AND TIME | 60, 90, 120 DAYS CONTROL | | 5/94 CONTROL DEVELOPMENT |
|---|---|---|---|---|---|---|
| 5/87 | 39 M | generalized lymphadenopathy fever homosexual, drug addict ELISA + WB + CD4 300 | 0.30 ml. 120 days | ELISA + CD4 800 | ELISA − CD4 900 | clinically cured |
| 6/87 | 60 M | lymphadenopathy diarrhea fever homosexual ELISA + WB + CD4 250 | 0.30 ml. 120 days | ELISA CD4 700 | WB − ELISA − CD4 850 | clinically cured |
| 7/87 | 41 M | lymphadenopathy fever, aphthae drug addict ELISA + CD4 400 | 0.30 ml. 120 days | ELISA − CD4 700 | ELISA − CD4 850 | clinically cured |
| 8/87 | 36 M | lymphadenopathy stress, fever drug addict ELISA + CD4 310 | 0.30 ml. 120 days | ELISA − CD4 700 | WB − ELISA − CD4 850 | clinically cured |
| 9/87 | 38 M | endogenous depression, apathy, drug addict homosexual ELISA + WB + CD4 350 | 0.30 ml. 120 days | ELISA − CD4 750 | WB − ELISA − CD4 830 | clinically cured |
| 10/87 | 22 F | lymphadenopathy fever prostitute ELISA + WB + CD4 300 | 0.30 ml. 120 days | ELISA − CD4 750 | WB − ELISA − CD4 840 | clinically cured |
| 11/87 | 44 M | lymphadenopathy fever, diarrhea bisexual ELISA + CD4 400 | 0.30 ml. 120 days | ELISA − CD4 850 | WB − ELISA − CD4 910 | clinically cured |
| 2/88 | 52 M | lymphadenopathy fever, post transfusion ELISA + CD4 350 | 0.30 ml. 120 days | ELISA − CD4 850 | ELISA − CD4 810 | clinically cured |
| 3/88 | 22 F | generalized discomfort, depression, raped by persons with AIDS ELISA + WB + CD4 300 | 0.30 ml. 120 days | ELISA − CD4 600 | ELISA − CD4 750 | stable |
| 3/89 | 28 M | depression, atted suicide, LAP fever, homosexual, drug addict ELISA + WB + CD4 400 | 0.30 ml. 120 days | ELISA − CD4 800 | ELISA − CD4 850 | clinically cured |
| 5/89 | 13 M | hemophilia infection ELISA + WB + CD4 300 | 0.30 ml. 120 days | ELISA − CD4 600 | ELISA − CD4 810 WB− | stable |
| 6/90 | 43 M | generalized lymph-adenopathy anorexia, fever, asthenia, bisexual ELISA + WB + CD4 350 | 0.30 ml. 120 days WB− | ELISA − CD4 800 | ELISA − CD4 850 | stable |
| 7/90 | 28 M | aphthae, convulsion, fever, homosexual, drug addict ELISA + WB + CD4 160 | 0.30 ml. 120 days | ELISA CD4 300 | ELISA − CD4 600 | stable |
| 2/90 | 40 F | anorexia, weight loss, fever, drug addict ELISA + WB + CD4 300 | 0.30 ml. 120 days | ELISA CD4 500 | ELISA − CD4 700 | stable |
| 3/90 | 45 M | LAP fever drug addict ELISA + WB + CD4 280 | 0.30 ml. 120 days | ELISA CD4 550 | ELISA − CD4 820 | stable |
| 11/90 | 70 M | LAP fever depression due to transfusion ELISA + WB + CD4 300 | 0.30 ml. 120 days | ELISA CD4 400 | ELISA − CD4 550 | stable |
| 3/91 | 21 F | LAP fever injectable drugs AIDS ELISA + CD4 500 | 0.30 ml. 120 days | ELISA CD4 700 | WB − ELISA CD4 830 | stable |
| 4/91 | 46 | aphthae, LAP asthenia, | 0.30 ml. 120 days | ELISA | ELISA − | stable |

TABLE 4-continued

TREATMENT WITH S.I.I.F. ON PATIENTS WITH ACQUIRED IMMUNODEFICIENCY SYNDROME (AIDS) TWENTY-TWO CASES OF ACQUIRED IMMUNODEFICIENCY SYNDROME (AIDS) HAVE BEEN TAKEN. SEVEN OF THEM TREATED SINCE 1987 AND THE OTHER FOURTEEN SINCE 1988 UNTIL THE PRESENT OF THE 200 CASES TREATED, 70% ARE CLINICALLY CURED AND 30% HAVE DIED (7% SUICIDES, 15% TUBERCULOUS MENINGITIS, 8% PNEUMONIA) IN ALL CASES WE ADDED THIOCTIC ACID, AND IN THE CASE OF INFECTIONS; BACTERIN AND ISONIAZID, ANTI-DIARRHEAL, AND IN DEPRESSIONS, IMPRAMIN WE DID NOT EMPLOY A.Z.T., D.D.C. OR D.D.I. (ALTHOUGH THE MAJORITY OF THE PATIENTS HAD TAKEN THOSE MEDICATIONS PREVIOUSLY) FINALLY, WE MUST CLARIFY THAT AFTER 120 DAYS, 40%, STABLE UNTIL THAT CONTROL POINT, FAIL TO RETURN

| DATE | AGE SEX | CLINICAL AND LABORATORY ASPECTS | S.I.I.F. TREATMENT DOSAGE AND TIME | 60, 90, 120 DAYS CONTROL | | 5/94 CONTROL DEVELOPMENT |
|---|---|---|---|---|---|---|
| | M | post trac., bisexual ELISA + WB + CD4 200 | | | CD4 400 | CD4 810 |
| 5/92 | 19 M | LAP fever depression homosexual ELISA + WB + CD4 300 | 0.30 ml. 120 days | ELISA CD4 60 | ELISA – WB – CD4 750 | stable |
| 4/92 | 23 F | lymphadenopathy fever, drug sexual promiscuity ELISA + CD4 360 | 0.30 ml. 120 days | ELISA CD4 420 | ELISA – CD4 730 | clinically cured |
| 5/93 | 42 M | diarrhea homosexual, drug addict ELISA + CD4 410 | 0.30 ml. 120 days | ELISA CD4 510 | ELISA – CD4 640 | stable |
| 12/91 | 55 M | LAP fever anorexia homosexual ELISA + WB + CD4 400 | 0.30 ml. 120 days | ELISA WB – CD4 600 | ELISA – WB – CD4 820 | stable |

ELISA = enzyme-linked immunosorbent assay.
LAP means lymphadenopathy.

In Table 4, the number of days in column 5 refers to the number of days after initiation of therapy. "Cured" means that CD4 counts are normal. In column 5 (60, 90, 120 days control), the last figure refers to 120 days. "0.30 ml. 120 days" means 0.30 ml of the composition prepared according to Example 1 administered daily for 120 days. "Stable" means no degeneration in CD4 counts.

Further variations and modifications of the foregoing will be apparent to those skilled in the art and such variations and modifications are attended to be encompassed by the claims that are appended hereto.

What is claimed is:

1. A pharmaceutical composition comprising a therapeutically active amount of phospholipase $A_2$ and giroxina in admixture with suitable inert pharmaceutical carriers or diluents.

2. The pharmaceutical composition according to claim 1, wherein the weight ratio of said phospholipase $A_2$ to said giroxina is between 20:1 and 4:1.

3. The pharmaceutical composition according to claim 2, wherein the weight ratio between said phospholipase $A_2$ and said giroxina is between 8:1 and 9:1.

4. The pharmaceutical composition according to claim 3, wherein the weight ratio between said phospholipase $A_2$ and said giroxina is about 8.1:1.

5. The pharmaceutical composition according to claim 1, wherein said phospholipase $A_2$ is isolated from the dried venom of *Crotalus durissus terrificus* or from the dried venom of *Micrurus frontalis altirostris*.

6. The pharmaceutical composition according to claim 1, wherein said giroxina is isolated from the dried venom of *Crotalus durissus terrificus*.

7. The pharmaceutical composition according to claim 5, wherein said giroxina is isolated from the dried venom of *Crotalus durissus terrificus*.

8. The pharmaceutical composition according to claim 1, wherein said inert pharmaceutical diluent is a sodium chloride solution.

9. The pharmaceutical composition according to claim 8, further containing a conservator.

10. The pharmaceutical composition according to claim 9, wherein said conservator is THIMEROSAL®.

11. The pharmaceutical composition according to claim 1, further containing tioctic acid.

12. The pharmaceutical composition according to claim 1, further containing magnesium lactate.

13. The pharmaceutical composition according to claim 1, further containing $B_6$ vitamin.

14. A process for the preparation of the pharmaceutical composition of claim 1 comprising admixing a therapeutically active amount of phospholipase $A_2$ and of giroxina with suitable inert pharmaceutical carriers or diluents.

15. The process according to claim 14, including dissolving and admixing said phospholipase $A_2$ and said giroxina in a sodium chloride solution.

16. The process according to claim 15 wherein said sodium chloride solution contains a conservator.

17. A method of increasing the CD4 count in a patient comprising administering to the patient in need thereof a composition consisting essentially of a therapeutically active amount of phospholipase $A_2$ and giroxina in admixture with an inert pharmaceutical carrier or diluent.

18. The method according to claim 17 wherein said composition contains said phospholipase $A_2$ and said giroxina in a weight ratio between 20:1 and 4.1.

19. The method according to claim 18, wherein said composition contains said phospholipase $A_2$ and said giroxina in a weight ratio between 8:1 and 9:1.

20. The method according to claim 19, wherein said composition contains said phospholipase $A_2$ and said giroxina in a weight ratio of about 8.1:1.

21. The method according to claim 17, wherein said phospholipase $A_2$ is isolated from the dried venom of *Crotalus durissus terrificus* or from the dried venom of *Micrurus frontalis altirostris*.

22. The method according to claim 17, wherein said giroxina is isolated from the dried venom of *Crotalus durissus terrificus*.

23. The method according to claim 17, wherein said inert pharmaceutical diluent is a sodium chloride solution.

24. The method according to claim 23, wherein said sodium chloride solution contains a conservator.

25. A method according to claim 24, wherein said conservator is thimerosal.

26. The method according to claim 17, wherein said composition further includes tioctic acid.

27. The method according to claim 17, wherein said composition further includes magnesium lactate.

28. The method according to claim 17, wherein said composition further includes $B_2$ vitamin.

* * * * *